United States Patent
Zilbershtein (10) Patent No.: US 9,975,822 B2
(45) Date of Patent: May 22, 2018

(54) METHODS OF PRECIPITATING POLYMER AND DEACTIVATED ORGANOMETALLIC CATALYST IN AN OLEFIN OLIGOMERIZATION REACTION

(71) Applicant: PUBLIC JOINT STOCK COMPANY "SIBUR HOLDING", Tobolsk (RU)

(72) Inventor: Timur Mikhailovich Zilbershtein, Kazan (RU)

(*) Notice: Subject to any disclaimer, the term of this patent is extended or adjusted under 35 U.S.C. 154(b) by 0 days. days.

(21) Appl. No.: 15/539,134

(22) PCT Filed: Dec. 23, 2014

(86) PCT No.: PCT/RU2014/000972
§ 371 (c)(1),
(2) Date: Jun. 22, 2017

(87) PCT Pub. No.: WO2016/105226
PCT Pub. Date: Jun. 30, 2016

(65) Prior Publication Data
US 2017/0349509 A1    Dec. 7, 2017

(51) Int. Cl.
*C07C 7/12* (2006.01)
*C07C 2/32* (2006.01)
(Continued)

(52) U.S. Cl.
CPC .............. *C07C 7/12* (2013.01); *B01J 31/143* (2013.01); *B01J 31/181* (2013.01); *C07C 2/32* (2013.01);
(Continued)

(58) Field of Classification Search
None
See application file for complete search history.

(56) References Cited

U.S. PATENT DOCUMENTS

2012/0142989 A1* 6/2012 Jaber .................. C07C 2/36
585/532
2012/0302715 A1    11/2012 Zilbershtein et al.

FOREIGN PATENT DOCUMENTS

RU    2 131 405    6/1999
RU    2 249 585    1/2004
(Continued)

OTHER PUBLICATIONS

International Search Report and Written Opinion dated Sep. 28, 2015, directed to International Application No. PCT/RU2014/000972; 8 pages.

*Primary Examiner* — Tam M Nguyen
(74) *Attorney, Agent, or Firm* — Morrison & Foerster LLP (57) ABSTRACT

A method of precipitating polymer and deactivated organometallic catalyst in an olefin oligomerization reaction is provided. The method includes providing an effluent stream from an olefin oligomerization reaction. The effluent stream can include a polymer and an organometallic catalyst. The method can further include introducing sorbent particles into the effluent stream. The sorbent particles can include a deactivating agent. The deactivating agent can be water, an alcohol, an amine, an amino alcohol, or a combination thereof. At least about 10% of the sorbent particles can have a particle size in a range from 10 μm and 60 μm. The method can further include cooling the effluent stream, thereby precipitating polymer and deactivated organometallic catalyst from the effluent stream to provide a precipitate that includes sorbent, polymer, and deactivated catalyst.

18 Claims, 5 Drawing Sheets

(51) Int. Cl.
*B01J 31/14* (2006.01)
*B01J 31/18* (2006.01)

(52) U.S. Cl.
CPC ........ *B01J 2231/20* (2013.01); *B01J 2531/62* (2013.01); *C07C 2531/14* (2013.01); *C07C 2531/18* (2013.01)

(56) References Cited

FOREIGN PATENT DOCUMENTS

| | | |
|---|---|---|
| WO | WO-2012/071644 | 6/2012 |
| WO | WO-2013/109371 | 7/2013 |
| WO | WO-2016/105227 | 6/2016 |
| WO | WO-2016/105228 | 6/2016 |

* cited by examiner

METHODS OF PRECIPITATING POLYMER AND DEACTIVATED ORGANOMETALLIC CATALYST IN AN OLEFIN OLIGOMERIZATION REACTION

REFERENCE TO RELATED APPLICATIONS

This application is a national stage application under 35 USC 371 of International Application No. PCT/RU2014/000972, filed Dec. 23, 2014, the entire contents of which are incorporated herein by reference.

BACKGROUND OF THE INVENTION

Field of the Disclosed Subject Matter

The presently disclosed subject matter relates to oligomerization of olefins. Particularly, the presently disclosed subject matter is directed to methods of precipitating polymer and deactivated organometallic catalyst in an olefin oligomerization reaction. The methods can include the use of sorbents to facilitate precipitation.

Description of Related Art

Oligomerization of olefins can produce many valuable chemical products. For example, simple feedstock olefins can be oligomerized to provide useful higher olefins. Industrially important processes include the preparation of alpha olefins (α olefins) from ethylene, e.g., the preparation of 1-hexene via trimerization of ethylene.

A problem encountered in some oligomerizations of olefins can be incomplete selectivity for the desired oligomer. That is, in addition to the desired oligomer, side products and byproducts can be formed. The side products and byproducts can include other oligomers as well as polymers. As an example, in oligomerization of ethylene to 1-hexene, other isomers of hexene (2-hexene and 3-hexene) can be formed, as well as higher oligomers of ethylene (e.g., octene, decene, and dodecene) and polyethylene.

Polymers formed as side products and byproducts during oligomerizations of olefins can be problematic. For example, on industrial scale, polymer can deposit on internal parts of oligomerization reactors and/or product pipelines, as well as other equipment that comes into contact with reaction and product mixtures. Moreover, polymer that remains dissolved in a product mixture must be separated from the desired oligomer product. As an example, in oligomerization of ethylene to 1-hexene, polyethylene can deposit on reactors and downstream equipment and can complicate purification of 1-hexene. It can therefore be beneficial to remove polyethylene from an effluent stream from an ethylene trimerization reaction.

An additional issue encountered in some oligomerizations of olefins can be the necessity of deactivating an active organometallic catalyst after the desired reaction is complete. Some organometallic catalysts can incorporate highly reactive organometallic bonds, e.g., metal-alkyl bonds. Such active metal species can react vigorously if exposed suddenly to water and/or oxygen. Such active metal species can also cause other problems if not deactivated after the desired reaction period is complete. For example, active metal species present in downstream effluents can catalyze unwanted reactions. Active organometallic catalysts can require controlled deactivation by a deactivating agent (e.g., water, an alcohol, an amine, an amino alcohol, or a mixture thereof) before a desired reaction product can be obtained from a reaction mixture containing the catalyst. Deactivated catalyst can then be removed from the reaction mixture.

Various attempts have been made to address removal of polymer and deactivation and removal of organometallic catalysts. Russian Patent Nos. RU2131405 and RU2249585, the contents of which are hereby incorporated by reference, describe addition of water to organometallic catalysts to deactivate the catalysts, providing hydrated metal oxides (e.g., hydrated oxides of aluminum and chromium), which can be precipitated from a reaction mixture. International (PCT) Application Publication Nos. WO2012/071644 and WO2013/109371, the contents of which are hereby incorporated by reference, describe use of sorbents (e.g., alumina and silica) to facilitate binding of oxide precipitates. Sorbents can also bind and precipitate polymers, facilitating their removal.

Addition of a deactivating agent (e.g., water and/or an alcohol) to a reaction mixture and subsequent addition of a sorbent can have drawbacks. For example, the deactivating agent can be added in a large excess relative to the organometallic catalyst, resulting in an effluent stream that is contaminated with the deactivating agent. Excess deactivating agent (e.g., water and/or an alcohol) must then be removed from the effluent stream, necessitating use of a drying agent or other methods.

It is therefore desirable to provide a method of precipitating polymer and deactivating organometallic catalyst in an olefin oligomerization reaction that does not require addition of an excess amount of deactivating agent and subsequent addition of a sorbent. It is further desirable to determine a preferred particle size for the sorbent so as to optimize precipitation of polymer and deactivated catalyst.

SUMMARY OF THE INVENTION

The purpose and advantages of the disclosed subject matter will be set forth in and apparent from the description that follows, as well as will be learned by practice of the disclosed subject matter. Additional advantages of the disclosed subject matter will be realized and attained by the methods and techniques particularly pointed out in the written description and the claims hereof, as well as from the appended drawings.

To achieve these and other advantages and in accordance with the purpose of the disclosed subject matter, as embodied and broadly described, the disclosed subject matter provides methods of precipitating side products, byproducts, and/or deactivated catalysts.

In accordance with the disclosed subject matter, a method of precipitating polymer and deactivated organometallic catalyst in an olefin oligomerization reaction is provided. The method can include providing an effluent stream from an olefin oligomerization reaction. The effluent stream can include a polymer and an organometallic catalyst. The method can further include introducing sorbent particles into the effluent stream. The sorbent particles can include a deactivating agent. The deactivating agent can be water, an alcohol, an amine, an amino alcohol, or a combination thereof. At least about 10% of the sorbent particles can have a particle size in a range from 10 μm and 60 μm. The method can further include cooling the effluent stream, thereby precipitating polymer and deactivated organometallic catalyst from the effluent stream to provide a precipitate that includes sorbent, polymer, and deactivated catalyst.

In accordance with some embodiments of the disclosed subject matter, the organometallic catalyst can include chromium.

In accordance with some embodiments of the disclosed subject matter, the olefin oligomerization reaction can include a trimerization of ethylene to 1-hexene.

In accordance with some embodiments of the disclosed subject matter, the sorbent particles can include particles that are alumina particles, silica particles, or a combination thereof. At least about 20% of the sorbent particles can have a particle size in a range from 10 μm to 60 μm. For example, about 40% of the sorbent particles can have a particle size in the range from 10 μm to 60 μm. The sorbent particles can include the deactivating agent in an amount less than about 20% by weight. For example, the sorbent particles can include the deactivating agent in an amount between about 5% and about 10% by weight. The sorbent particles can have a surface area greater than 10 $m^2/g$.

In accordance with some embodiments of the disclosed subject matter, the sorbent particles can be introduced into the effluent stream as a suspension in a solvent. The sorbent particles can be introduced into the effluent stream in an amount between about 0.1 g and about 1.0 g of the sorbent particles per 1 kg of the effluent stream. The deactivating agent can include water.

In accordance with some embodiments of the disclosed subject matter, the effluent stream can be cooled at about the same time that the sorbent particles are introduced into the effluent stream. Alternatively, the effluent stream can be cooled after the sorbent particles are introduced into the effluent stream.

In accordance with some embodiments of the disclosed subject matter, the precipitate can include precipitate particles having a particle size in a range from about 1 μm to about 1000 μm. In some embodiments, less than about 8% of the precipitate particles can have a particle size of less than 10 μm. In some embodiments, less than about 0.8% of the precipitate particles can have a particle size of less than 5 μm.

In accordance with some embodiments of the disclosed subject matter, the method of precipitating polymer and deactivated organometallic catalyst in an olefin oligomerization reaction can further include separating the precipitate from the effluent stream to provide a purified product.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

While the disclosed subject matter is described below in detail with reference to the Figures, it is done so in connection with the illustrative embodiments and not by way of limitation.

DETAILED DESCRIPTION OF THE INVENTION

The methods presented herein can be used for various oligomerization processes, including, but not limited to, olefin oligomerizations, e.g., trimerization or tetramerization of ethylene. The methods can be used on relatively small scale, e.g., laboratory scale or bench scale, and can be used on relatively large scale, e.g., industrial scale. Oligomerization can occur in a homogeneous or colloidal solution. Oligomerization can occur in various reactors known in the art, as described in more detail below. Oligomerization can occur in more than one reactor operated in series or parallel. For purpose of illustration only and not limitation, and as embodied herein, the methods presented can be used in the context of trimerization of ethylene to 1-hexene.

As used herein, the term "alkyl" refers to saturated aliphatic groups. Alkyl groups can be straight chain (e.g., ethyl, n-propyl, n-butyl) or branched chain (e.g., i-propyl, s-butyl). The term "alkyl" also encompasses cycloalkyl groups, i.e., saturated aliphatic carbon-based cyclic groups. Cycloalkyl groups can include one ring or more than one ring. By way of non-limiting example, cycloalkyl groups can include cyclopropyl, cyclobutyl, cyclopentyl, cyclohexyl, cycloheptyl, and cyclooctyl.

As used herein, the terms "alkane" and "alkanes" refer to saturated aliphatic compounds. Alkyl compounds can be straight chain (e.g., ethane, propane, n-butane, n-hexane, n-octane, n-decane) or branched chain (e.g., i-butane, 3-methylnonane). Straight chain alkanes are also known as linear alkanes or n-alkanes and are acyclic alkanes without side chains. Branched chain alkanes, also known simply as "branched alkanes," are acyclic, non-linear alkanes with one or more side chains.

As used herein, the terms "alkane" and "alkanes" also encompass cycloalkane compounds, i.e., saturated aliphatic carbon-based cyclic compounds. Cycloalkanes can include one ring or more than one ring. By way of non-limiting example, cycloalkanes can include cyclopropane, cyclobutane, cyclopentane, cyclohexane, cycloheptane, cyclooctane, cyclononane, and cyclodecane. Cycloalkanes can be substituted. Exemplary substituted cycloalkanes include methylcyclopentane and methylcyclohexane.

As used herein, the term "halogen" refers to the Group 17 elements, i.e., fluorine, chlorine, bromine, iodine, and astatine.

As used herein, the terms "group" and "moiety" refer to parts of a larger composition, compound, molecule, or structure.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

In accordance with the disclosed subject matter, methods of precipitating polymer and deactivated organometallic catalyst in an olefin oligomerization reaction can generally include providing an effluent stream from an olefin oligomerization reaction. The effluent stream can include a polymer and an organometallic catalyst. The method can further include introducing sorbent particles into the effluent stream. The sorbent particles can include a deactivating agent. The deactivating agent can be water, an alcohol, an amine, an amino alcohol, or a combination thereof. At least about 10% of the sorbent particles can have a particle size in a range from 10 μm and 60 μm. The method can further include cooling the effluent stream, thereby precipitating polymer and deactivated organometallic catalyst from the effluent stream to provide a precipitate that includes sorbent, polymer, and deactivated catalyst.

Reference will now be made in detail to the various exemplary embodiments of the disclosed subject matter, exemplary embodiments of which are illustrated in the accompanying drawings. The methods and corresponding techniques of the disclosed subject matter will be described in conjunction with the detailed description.

The accompanying figures serve to further illustrate various embodiments and to explain various principles and advantages all in accordance with the disclosed subject matter. For purpose of explanation and illustration, and not limitation, exemplary embodiments of the method of precipitating polymer and deactivated organometallic catalyst in an olefin oligomerization reaction in accordance with the disclosed subject matter are shown in FIGS. 1-5. While the presently disclosed subject matter is described with respect to the system of FIG. 1 and the Examples presented below, one skilled in the art will recognize that the disclosed subject matter is not limited to the illustrative embodiments, and that the methods and techniques described herein can be used to precipitate polymer and deactivated organometallic catalyst in any suitable reaction or system.

Figure 1:
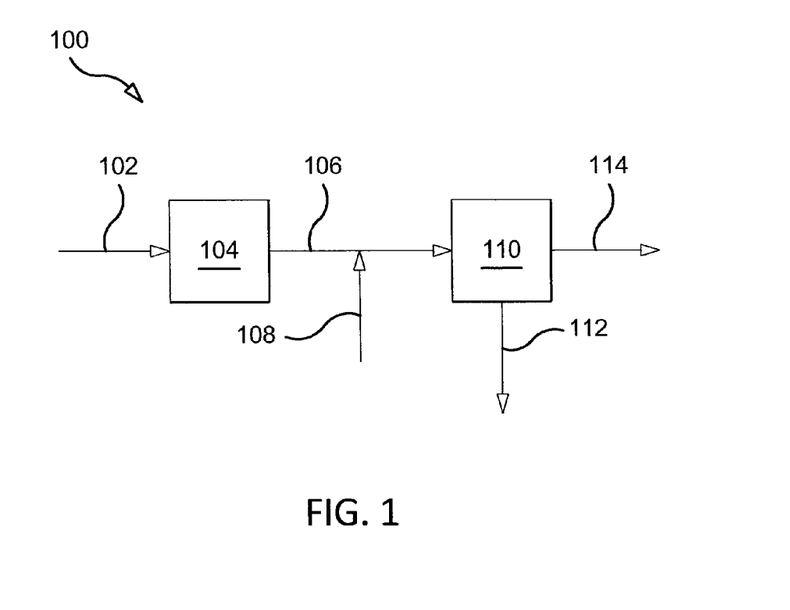
FIG. 1 is a schematic representation illustrating an exemplary system that can be used in conjunction with the methods of the disclosed subject matter.

In accordance with the disclosed subject matter, with reference to FIG. 1, the presently disclosed methods can be performed in conjunction with an exemplary system 100. The system 100 can include a reactor 104 in which an olefin oligomerization reaction can be conducted. The reactor 104 can be coupled to one or more feed lines 102. While one feed line 102 is shown in FIG. 1, it should be understood that multiple feed lines can be coupled to the reactor 104. The feed line(s) 102 can feed various components to the reactor 104. In some embodiments, the components fed to the reactor 104 can include an organometallic catalyst, a transition metal source, an alkylaluminum compound, a zinc compound, a pyrrole compound, a halogenic compound, an olefin, hydrogen, and/or a solvent. By way of non-limiting example, in some embodiments there can be one or more feed lines feeding an organometallic catalyst solution, one or more feed lines feeding solvent(s), one or more feed lines feeding an olefin (e.g., ethylene), and/or one or more feed lines feeding hydrogen. In some embodiments, more than one hydrocarbon compound can be used as solvent, and different mixtures of solvent can be used to prepare various compositions. For example, in some embodiments, a first solvent can be used as a catalyst solvent (e.g., a solvent used to dissolve an alkylaluminum compound, a chromium compound, and additional catalyst components) and a second solvent can be added as an additional reaction solvent. All solvents can be combined in the reactor 104 to provide a combined reaction solvent.

An olefin oligomerization reaction can occur in the reactor 104, to provide oligomerization products as well as side product polymer. An effluent stream 106 containing oligomerization products, polymer, and organometallic catalyst can be removed from the reactor 104. Sorbent particles 108 can be introduced into the effluent stream 106 to deactivate the organometallic catalyst, and the effluent stream 106 can be cooled, thereby precipitating polymer and deactivated organometallic catalyst. Precipitate containing sorbent, polymer, and deactivated catalyst can optionally be separated in a separation unit 110, to provide precipitate 112 and a purified product stream 114.

The olefin oligomerization reactions of the presently disclosed subject matter can performed in various reactors known in the art. By way of non-limiting example, suitable reactors 104 can include continuous stirred-tank reactors, batch reactors, plug flow reactors, and pipe or tubular reactors (laminar flow reactors). The reactor 104 can be a reactor suitable for gas/liquid reactions, e.g., an autoclave reactor with an agitator, a bubble column reactor (bubbling reactor) with straight-flow or counter-flow gas and liquid supply, or a bubbling gas lift reactor. The reactor can include components and accessories not depicted in FIG. 1, such as, for example, one or more additional feed lines, one or more gas inlet lines, one or more gas outlet lines, one or more flue gas exhaust lines, one or more agitators, a reaction zone, one or more heating elements, and/or one or more viscometers. The components and accessories can be placed at various locations on the reactor, as known in the art.

In some embodiments, the organometallic catalyst in the reactor 104 can include one or more transition metal sources. By way of non-limiting example, the transition metal(s) can be Ti, Zr, Hf, Ni, Cr, Fe, Co, Pd, Pt, and combinations thereof. In accordance with the disclosed subject matter, the organometallic catalyst can include chromium (Cr). The organometallic catalyst can be a homogenous catalyst or a heterogeneous catalyst.

When the organometallic catalyst includes chromium, the source of chromium can be organic and/or inorganic. The oxidation state of the chromium source can vary. For example, chromium sources can include compounds in which chromium is in the oxidation states 0, +1, +2, +3, +4, +5, and +6. Generally, the chromium source can be of the formula $CrX_n$, where the X substituents are the same or different and where n is a number from 1 to 6. The X substituents can be organic or inorganic radicals. By way of non-limiting example, suitable organic radicals X can include from 1 to 20 carbon atoms and can include alkyl groups, alkoxy groups, carboxy groups, acetylacetonate groups, amino groups, and amido groups. By way of non-limiting example, suitable inorganic radicals X can include halogens (to form a chromium halide), sulfate (to form a chromium sulfate), and oxygen (to form a chromium oxide). Examples of chromium sources can include chromium(III) chloride, chromium(III) acetate, chromium(III) tris-ethylhexanoate, chromium(III) acetylacetonate, chromium(III) pyrrolide, chromium(II) acetate, and chromyl chloride ($CrO_2Cl_2$).

The organometallic catalyst in the reactor 104 can further include an alkylaluminum compound. In some embodiments, the alkylaluminum compound can be an activator of a transition metal-based catalyst center (e.g., a chromium center). Alkylaluminum compounds can include halogenated alkylaluminum compounds, alkoxyalkylaluminum compounds, and mixtures thereof. Alkylaluminum compounds are compounds that include at least one aluminum-alkyl bond and, in some nonlimiting embodiments, can be represented by the general formulas $AlR_3$, $AlR_2X$, $AlRX_2$, $AlR_2OR$, $AlRXOR$, or $Al_2R_3X_3$, where R is an alkyl group and X is a halogen atom (e.g., Cl or Br). Nonlimiting examples of alkylaluminum compounds include trimethylaluminum, triethylaluminum, tripropylaluminum, tributylaluminum, diethylaluminum chloride, ethylaluminum dichloride, ethylaluminum sesquichloride, and methylaluminoxane (MAO). Alkylaluminum compounds can be used as mixtures of multiple alkylaluminum compounds. In some embodiments, the alkylaluminum compound can be triethylaluminum or a mixture of triethylaluminum and diethylaluminum chloride.

In accordance with the disclosed subject matter, one or more components of the organometallic catalyst in the reactor 104 can be irradiated. In some embodiments, the alkylaluminum compound can be an irradiated alkylaluminum compound. Alkylaluminum compounds can be irradiated to increase their activity and to increase the overall activity of the organometallic catalyst in the reactor 104. In some embodiments, the irradiation can be microwave irradiation. Microwave irradiation of alkylaluminum compounds is generally described in United States Patent Publication No. 2012/0302715, the contents of which are hereby incorporated by reference. By way of non-limiting example, one or more alkylaluminum compounds can be irradiated with microwave radiation of a frequency between about 0.2 GHz and 20 GHz. In some embodiments, the microwave radiation can have a frequency of about 2.45 GHz. The duration of irradiation can be between about 0.5 minutes (30 seconds) and about 20 minutes. In some embodiments, one or more alkylaluminum compounds can be irradiated with microwave radiation prior to mixing with other components of the catalyst composition (e.g., a transition metal source). If the alkylaluminum compound is irradiated prior to mixing with other components of the catalyst composition, it can be important to limit the time that elapses between irradiation and mixing. For example, the time can be less than 10 minutes, less than 5, or less than 3 minutes. In some embodiments, the time between irradiation of the alkylaluminum compound and mixing with other components of the catalyst composition (e.g., a transition metal source) can be less than 3 minutes. In other embodiments, one or more alkylaluminum compounds can first be combined with a transition metal source (e.g., a chromium source) and a pyrrole compound to provide a composition, and the composition can then be irradiated as described above. Further description of irradiation of alkylaluminum compounds and other catalyst components, in accordance with the disclosed subject matter, is provided in International (PCT) Application No. PCT/RU2014/000973, filed Dec. 23, 2014, which is hereby incorporated by reference in its entirety.

The organometallic catalyst in the reactor 104 can further include one or more halogenic compounds. The halogenic compound can be described as a halide source. The halogenic compounds can be compounds of formula $R_mX_n$, wherein R is an organic, organometallic, or inorganic radical, X is a halogen (e.g., F, Cl, Br, or I), and the sum (m+n) is greater than 0. Exemplary halogenic compounds can include $AlEt_2Cl$, $AlEtCl_2$, $AlCl_3$, dibutylaluminum chloride, diethylaluminum bromide, diethylaluminum iodide, butyl bromide, dichloromethane, carbon tetrachloride, $CHCl_3$ (chloroform), hexachloroethane, boron trichloride, and germanium tetrachloride. Addition of one or more halogenic compounds can improve the selectivity, activity, and/or productivity of the organometallic catalyst.

The organometallic catalyst in the reactor 104 can further include a zinc compound. In some embodiments, the zinc compound can be an activator of a transition metal-based catalyst center (e.g., a chromium center). In some embodiments, the zinc compound can include metallic zinc (Zn(0)), zinc-copper couples, alkylzinc compounds (including dialkylzinc compounds), arylzinc compounds (including diarylzinc compounds), zinc amides (e.g., zinc pyrrolides or zinc porphyrin complexes), zinc oxygenates (e.g., zinc formates, zinc acetates, zinc 2-ethylhexanoates, and other zinc carboxylates), zinc halides (e.g., anhydrous zinc chloride), and combinations thereof. In some embodiments, the zinc compound can include a dialkylzinc compound. In some embodiments, the dialkylzinc compound can include dimethylzinc, diethylzinc, dibutylzinc, and mixtures thereof. In some embodiments, the zinc compound can include a diarylzinc compound. In some embodiments, the diarylzinc compound can include diphenylzinc, ditolylzinc, and mixtures thereof.

The organometallic catalyst in the reactor 104 can further include a pyrrole compound. In some embodiments, the pyrrole compound can coordinate to a transition metal and serve as a ligand. The pyrrole compound can be a compound that includes a pyrrole moiety, i.e., a five-membered aromatic heterocycle that contains a single nitrogen atom. By way of non-limiting example, pyrrole compounds include pyrrole, 2,5-dimethylpyrrole, lithium pyrrolide ($C_4H_4NLi$), 2-ethylpyrrole, indole, 2-methylindole, and 4,5,6,7-tetrahydroindole. In some embodiments, the pyrrole compound can be pyrrole or 2,5-dimethylpyrrole.

The organometallic catalyst in the reactor 104 can be varied, as is understood in the art. For example, when an alkylaluminum compound, a chromium compound, and a pyrrole compound are used, the molar ratios of aluminum to chromium and pyrrole compound to chromium can be varied. For example, and as embodied herein, the aluminum to chromium ratio can vary from about 10:1 to about 2000:1, e.g., from about 20:1 to about 300:1. For example, and as embodied herein, the pyrrole compound to chromium ratio can vary from about 2:1 to about 100:1, e.g., from about 3:1 to about 7:1. For example, and as embodied herein, the ratio of any additional halogenic compound to chromium can vary from about 1:1 to about 150:1, e.g., from about 8:1 to about 16:1, as calculated on the basis of elemental halogen. A zinc compound may or may not be included.

Olefins useful for olefin oligomerization can include simple feedstock olefins, e.g., ethylene (ethene), propylene (propene), and butylene (butene). In some embodiments, the olefin can be ethylene. Olefins can be oligomerized to provide useful higher olefins. Industrially important processes include preparation of alpha olefins (α olefins) from ethylene. Alpha olefins are olefin compounds with a carbon-carbon double bond (C=C) at the primary or alpha position. Alpha olefins prepared from oligomerization can include various $C_5$-$C_{40}$ olefins and mixtures thereof. For example, alpha olefins prepared from oligomerization can include 1-pentene, 1-hexene, 1-heptene, 1-octene, 1-nonene, 1-decene, 1-undecene, 1-dodecene, 1-tridecene, 1-tetradecene, higher alpha olefins, and mixtures thereof. In accordance with the disclosed subject matter, the olefin oligomerization reaction can include a trimerization of ethylene to 1-hexene.

When the olefin oligomerization in the reactor 104 is a trimerization of ethylene to 1-hexene, the pressure of ethylene used is variable, as is understood in the art. For example, and as embodied herein, the ethylene pressure can be varied between about 1 to about 200 bar. In some embodiments, the ethylene pressure can be greater than 4 bar. In some embodiments, in can be advantageous to increase the ethylene pressure to increase the rate of oligomerization.

In some embodiments of the presently disclosed subject matter, the temperature with the reactor 104 can be between about 0° C. and about 160° C. In some embodiments, the temperature within the reactor 104 can be between about 40° C. and about 120° C. For example, when the olefin oligomerization in the reactor 104 is a trimerization of ethylene to 1-hexene, the temperature of the reactor can be between about 40° C. and about 120° C., e.g., at about 100° C. In some embodiments, and as described herein, it can be advantageous to maintain a reaction temperature above about 80° C., e.g., above about 95° C. At such temperatures, polymer side products (e.g., polyethylene) can remain fully dissolved in the solvent and the organometallic catalyst can remain active and selective. By way of non-limiting example, in some trimerization reactions of ethylene to 1-hexene, lower temperatures (e.g., temperatures below about 80° C.) can cause polyethylene to precipitate from solution.

In accordance with the disclosed subject matter, reaction time can be varied as understood in the art. The reaction time can be defined as the residence time of the feedstock and solvent in the oligomerization reaction zone. In the case of continuous flow reactors, the reaction time can be the mean residence time, as understood in the art. The reaction time can vary depending on olefin used, reaction temperature, reaction pressure, and other parameters of the reaction. In some embodiments, the reaction can be terminated in less than a day. In some embodiments, reaction time can be shorter, e.g., less than 12 hours, less than 6 hours, less than 3 hours, less than 2 hours, less than 1 hour, less than 30 minutes, less than 15 minutes, less than 10 minutes, less than 5 minutes, less than 3 minutes, less than 2 minutes, less than 1 minute, less than 30 seconds, less than 15 seconds, less than 10 seconds, less than 5 seconds, less than 3 seconds, or about 1 second.

In accordance with the disclosed subject matter, an olefin and a catalyst composition (e.g., a composition that includes an alkylaluminum compound, a chromium compound, and a hydrocarbon solvent) can be contacted with hydrogen. Hydrogen can be fed into the reactor 104. In some embodiments, hydrogen can serve as a diluent. Hydrogen can accelerate the oligomerization reaction and/or increase activity of the organometallic catalyst. In some embodiments, hydrogen can reduce the amount of side product polymer formed and limit deposition (precipitation) of polymer with the reactor 104 and in downstream equipment. For example, in the oligomerization of ethylene to 1-hexene, hydrogen can reduce formation of polyethylene and discourage deposition of polyethylene.

One or more solvents can be used in oligomerization of olefins in the reactor 104. The solvent can include one or more hydrocarbon compounds. The hydrocarbon compounds can include alkane compounds, including straight chain alkanes, branched alkanes, and cycloalkanes. The hydrocarbon compounds can also include alkene compounds (e.g., 1-hexene) and/or arene (aromatic) compounds (e.g., benzene, toluene). The hydrocarbon compounds can be a mixture of hydrocarbons, e.g., kerosene. The hydrocarbon compounds can be C4-C12 hydrocarbons. By way of non-limiting example, the solvent can include cyclohexane, methylcyclohexane, heptane (and isomers thereof), cycloheptane, octane (and isomers thereof), cyclooctane, nonane (and isomers thereof), cyclononane, decane (and isomers thereof), cyclodecane, undecane (and isomers thereof), cycloundecane, dodecane (and isomers thereof), cyclododecane, and combinations thereof. Further description of solvents that can be used in accordance with the disclosed subject matter is provided in International (PCT) Application No. PCT/RU2014/000974 filed Dec. 23, 2014, which is hereby incorporated by reference in its entirety. In some embodiments, solvents can be preheated prior to use. For example, solvents can be preheated to a temperature approximately equal to the reaction temperature, e.g., about 100° C.

In accordance with the disclosed subject matter, in some embodiments components of the solvent(s) used can be selected on the basis of their boiling points. For example, alkane compounds having similar boiling points, which can boil within a relatively narrow temperature range (e.g., within about 10° C., about 20° C., about 30° C., or about 40° C.) can be used. Selection of alkane compounds having similar boiling points can facilitate separation, as such compounds can be conveniently distilled away from desired olefin oligomerization products (e.g., 1-hexene). Various mixtures of alkane compounds with similar boiling points can be commercially available, e.g., EXXSOL™ (EXXONMOBIL™) and ISOPAR™ (EXXONMOBIL™).

In accordance with the disclosed subject matter, various components present in the reactor 104 can be mixed in any order. By way of non-limiting example, an alkylaluminum compound can be mixed with a halogenic compound in a first hydrocarbon solvent to provide a first composition. The first mixture can be mixed with a transition metal source (e.g., a chromium source) and a pyrrole compound in a second hydrocarbon solvent to provide a second composition, which can serve as an organometallic catalyst. The first hydrocarbon solvent and the second hydrocarbon solvent can be the same or different. An olefin can then be contacted with the second composition to form oligomers of the olefin. Alternatively, the second composition can be further diluted in a third hydrocarbon solvent to provide a third composition, and an olefin can be contacted with the third composition.

In accordance with the disclosed subject matter, olefin oligomerization reactions can be conducted in the absence of water and oxygen. For example, water and oxygen can be excluded from the reactor 104.

In accordance with the disclosed subject matter, the effluent stream 106 from the olefin oligomerization reaction can include an organometallic catalyst, various products, byproducts, and side products from the olefin oligomerization reaction, and a solvent.

In some embodiments, polymers formed during olefin oligomerization can include polymers of the olefin being oligomerized. For example, polyethylene can form during oligomerization of ethylene. Polyethylene can be insoluble in the reaction solvent and can deposit on internal parts of oligomerization reactors and/or product pipelines, as well as other equipment that comes into contact with reaction and product mixtures. Moreover, polymer that remains dissolved in an oligomerization product mixture can require separation from the desired oligomer product.

Sorbents 108 useful in the methods of the present disclosure can include various solid materials. By way of non-limiting example, sorbents can include clays (both natural and synthetic), charcoal, silica, alumina, titania, magnesia, zirconia, aluminosilicates, zeolites, molecular sieves, diatomaceous earth, cellulosic materials, metal salts (e.g., calcium chloride, magnesium chloride, calcium sulfate, magnesium sulfate, and sodium sulfate), metal oxides (e.g., calcium oxide and magnesium oxide), and combinations thereof. In accordance with the disclosed subject matter, the sorbent particles can include alumina particles, silica particles, or a combination thereof.

In some embodiments, the sorbent 108 used can have a particle size in a range from about 10 μm to about 150 μm. For example, at least a portion of the sorbent particles can have a particle size in a range from about 10 μm to about 60 μm, e.g., from 30 μm to 60 μm. Sorbent particles with a particle size in a range from 10 μm to 60 μm, e.g., from 30 μm to 60 μm, can have advantageous properties, as described below. In accordance with some embodiments of the disclosed subject matter, at least about 20% of the sorbent particles can have a particle size in a range from 10 μm to 60 μm. For example, at least about 40%, 60%, 80%, or 90% of the sorbent particles can have a particle size in the range from 10 μm to 60 μm.

An advantage of using sorbent particles 108 with a particle size in a range from 10 μm to 60 μm in accordance with the disclosed subject matter can be that such particles are relatively slow to settle and remain suspended in a liquid mixture, where they can adsorb and remove polymer and/or deactivated catalyst from the liquid mixture. By way of non-limiting example, particles in a size range from about 10 μm to about 60 μm can remain suspended in a hydrocarbon solvent (e.g., an alkane) for approximately one minute or longer. By contrast, particles of larger particle size can settle more quickly, which can make them less effective at adsorbing dissolved polymer and/or deactivated catalyst. Particles with very small particle size (e.g., smaller than 10 μm) can have disadvantages. For example, sorbent particles smaller than 10 μm can clog filtration devices or require an impractically long time to settle.

In accordance with some embodiments of the disclosed subject matter, the sorbent particles 108 can include the deactivating agent in an amount less than about 20% by weight. For example, the sorbent particles can include the deactivating agent in an amount between about 5% and about 10% by weight. In some embodiments, the sorbent particles can be used "off the shelf," as obtained from commercial sources, without addition of additional deactivating agent and without treatment to remove deactivating agent. For example, in some embodiments, silica or alumina can be used without addition of water and without drying. The amount of water present in commercial sources of silica and alumina, which can be in a range from about 5% to about 10%, by weight, can be suitable for the methods of the present disclosure. When the deactivating agent is water, the amount of water present in a sorbent can be determined by thermal analysis. By way of non-limiting example, water content can be measured by heating the sorbent from 25° C. to 800° C. and determining the percentage of weight lost.

In some embodiments, sorbents 108 can be selected for high active surface area and/or large pore volume. Sorbents with high active surface area and large pore volume can have improved ability to adsorb both metal oxides and polymeric materials. In some embodiments, the sorbent particles can have a surface area greater than 0.1 m$^2$/g, e.g., greater than 0.3 m$^2$/g, greater than 0.5 m$^2$/g, greater than 1 m$^2$/g, greater than 3 m$^2$/g, greater than 5 m$^2$/g, or greater than 10 m$^2$/g. In accordance with the disclosed subject matter, the sorbent particles have a surface area greater than 10 m$^2$/g. In some embodiments, the sorbent particles can have pore volume of greater than 0.01 cm$^3$/g.

In accordance with the disclosed subject matter, the sorbent particles 108 can be introduced into the effluent stream 106 as a suspension in a solvent. For example, sorbent particles can be introduced as a suspension in a hydrocarbon solvent, e.g., a suspension in cyclohexane. In some embodiments, the solvent used to suspend the sorbent can be the same solvent used for the olefin oligomerization reaction. Suitable suspensions can include various amounts of sorbent, e.g., less than about 0.5% sorbent, about 0.5% sorbent, about 1% sorbent, about 2% sorbent, about 3% sorbent, about 4% sorbent, about 5% sorbent, about 6% sorbent, about 7% sorbent, about 8% sorbent, about 9% sorbent, about 10% sorbent, about 12% sorbent, about 15% sorbent, or about 20% sorbent, by weight. A suspension of a sorbent 108 can be pumped into an effluent stream 106, e.g., into a reaction mixture removed from an olefin oligomerization reactor 104.

In accordance with the disclosed subject matter, the sorbent particles 108 are introduced into the effluent stream 106 in an amount between about 0.1 g and about 1.0 g of the sorbent particles per 1 kg of the effluent stream. By way of nonlimiting example, and as embodied herein, about 0.1 g, about 0.2 g, about 0.3 g, about 0.4 g, about 0.5 g, about 0.6 g, about 0.7 g, about 0.8 g, about 0.9 g, or about 1.0 g of sorbent particles can be introduced per 1 kg of effluent stream.

Suitable deactivating agents known to one of skill in the art can be used, including water, alcohols, amines, amino alcohols, and combinations thereof. Exemplary alcohols can include methanol, ethanol, n-propanol, i-propanol, n-butanol, i-butanol, t-butanol, 2-butanol, 2-ethylhexanol, and combinations thereof. Exemplary amines can include ammonia, methylamine, dimethylamine, trimethylamine, ethylamine, diethylamine, triethylamine, tri-n-propylamine, diisopropylethylamine, tri-n-butylamine, piperazine, pyridine, ethylenediamine, diethylenetriamine, and combinations thereof. Exemplary amino alcohols can include ethanolamine, diethanolamine, triethanolamine, methyldiethanolamine, dodecyldiethanolamine, 1-amino-2-propanol, and combinations thereof. In accordance with the disclosed subject matter, the deactivating agent can be water. One or more deactivating agents can be added to the effluent stream 106 separately from the sorbent 108. However, and as embodied in the Examples, addition of a deactivating agent separate from the sorbent is not required.

In some embodiments, the effluent stream 106 can be cooled at about the same time that the sorbent particles 108 are introduced. Alternatively, the effluent stream can be cooled before the sorbent particles are introduced, or the effluent stream can be cooled after the sorbent particles are introduced. By way of non-limiting example, the sorbent particles can be introduced when the effluent stream is at a temperature in a range from about 65° C. to about 130° C., e.g., about 75° C. to about 115° C. or about 85° C. to about 105° C.

Cooling the effluent stream can include removing the effluent stream from a heat source, e.g., removing the effluent stream from a heated reactor. Cooling the effluent stream can also include passing the effluent stream through a cooling unit, e.g., a heat exchanger. Cooling the effluent stream can include mixing a hot effluent stream with a cooled effluent stream. Cooling the effluent stream can include cooling the effluent stream to a temperature in a range between about 100° C. and 20° C., e.g., to less than about 95° C., about 90° C., about 85° C., about 80° C., about 75° C., about 70° C., about 65° C., about 60° C., about 55° C., about 50° C., about 45° C., about 40° C., about 35° C., about 30° C., or about 25° C. Cooling the effluent stream can include exposing the effluent stream to air. Cooling the effluent stream can include cooling the effluent stream to ambient temperature, e.g., to a temperature in a range from about 20° C. to about 25° C. The temperature to which the effluent stream is cooled can be selected to induce precipitation of the polymer while also avoiding excessive energy consumption during the cooling process. By way of non-limiting example, the effluent stream can be cooled from about 110° C. to about 70° C. in a settler-cooler, via recycling in a loop cooling stream with a temperature of about 40° C. and a residence time in the settler-cooler of about 1 hour. The speed with which the effluent stream is cooled can have some effect on the particle size of polymer precipitate. For example, more rapid cooling can cause polymer to precipitate with smaller particle size.

In accordance with some embodiments of the disclosed subject matter, the precipitate can include precipitate particles having a particle size in a range from about 1 μm to about 1000 μm (1 mm). In some embodiments, and as illustrated in the Examples provided below, less than about 8% of the precipitate particles can have a particle size of less than 10 μm. In some embodiments, and as illustrated in the Examples provided below, less than about 0.8% of the precipitate particles can have a particle size of less than 5 μm. Reduction in the quantity of precipitate particles with a particle size below 10 μm and below 5 μm can improve the overall efficiency of olefin oligomerization and product purification.

In accordance with the disclosed subject matter, the methods of precipitating polymer and deactivated organometallic catalyst in an olefin oligomerization reaction can further include separating the precipitate from the effluent stream 106 to provide a purified product 114. Separation can provide separated precipitate 112 as well as the purified product 114. Separation can be performed via a separation unit 110. In some embodiments, the separation unit can be one or more settling tanks, centrifugal separators, or filters, or a combination thereof. For example, and as embodied herein, precipitate can be concentrated in one or more settling tanks and periodically unloaded. Centrifugal separators can also be used to separate precipitate, with or without earlier concentration. Filtration can also be used to separate precipitate, with or without earlier concentration.

By way of non-limiting example, the effluent stream 106 can be cooled and solids (e.g., polymer and sorbent) settled under pressure. The effluent stream can then be filtered and sent to a deethenizer column, which can remove ethylene and hydrogen and send them to a recycling compressor. The filtered and degassed effluent can then be sent to a product isolation column, where 1-hexene can be distilled and isolated as the top product. Heavier compounds, including solvent and higher olefins, can be removed from the bottom of the product isolation column.

The disclosed subject matter can provide olefin oligomers (e.g., 1-hexene) with very low levels of metal contamination. For example, an olefin oligomer can be obtained from the purified product 114 with less than 1 ppm levels of chromium, zinc, and aluminum.

EXAMPLES

The presently disclosed subject matter will be better understood by reference to the following Examples, which are provided as exemplary and not by way of limitation.

All particle size measurements described in the Examples below were made by laser light scattering, using a HORIBA LA-950V2 particle size analyzer.

Example 1

Catalyst Preparation:

A catalytic system was prepared by combining a chromium compound, an alkylaluminum compound, a pyrrole compound, and a solvent to provide a catalyst composition. A sample of 460 milligrams of chromium(III) ethylhexanoate as a 70% solution by weight in kerosene was combined with 2,5-dimethylpyrrole (DMP), triethylaluminum (TEA) and diethylaluminum chloride (DEAC), in a molar ratio of 1:5:30:14. Ethylbenzene in an amount of 50 mL was used as a solvent for the catalyst composition. TEA was used as a solution in toluene with a concentration of 1.9 M. DEAC was used as a solution in hexanes with a concentration of 1M. The TEA and DEAC solutions were first mixed together to provide a combined alkylaluminum solution and then added in one portion to the mixture of chromium (III) ethylhexanoate and DMP. After mixing for 15 minutes, the solvents were evaporated to dryness at 30-40° C. and 5 mbar, providing a residue. The residue was then diluted with cyclohexane to a concentration of 2 mg Cr/mL.

Oligomerization Reaction:

A steel 1.0 liter reactor equipped with a thermostatic jacket and ethylene and hydrogen supply lines was provided. The reactor was evacuated, and then filled with hydrogen to a pressure of 0.1 barg. The reactor was then loaded with 400 g of undecane using a dosing pump. The catalyst composition (1 mg of Cr) as a solution in cyclohexane (0.5 ml) with a concentration of 2 mg Cr/mL was added into the reactor under a counter-flow of hydrogen with the use of a syringe. Stirring at 800 rpm was started with the use of a propeller stirrer. Hydrogen was dosed to a pressure of 0.1 barg. Then, ethylene was dosed to a pressure of 12.1 barg. During the reaction, the reactor temperature was maintained at 100° C. with the use of a thermostat, and ethylene was dosed continuously to maintain a pressure of 12.1 barg.

Figure 2:
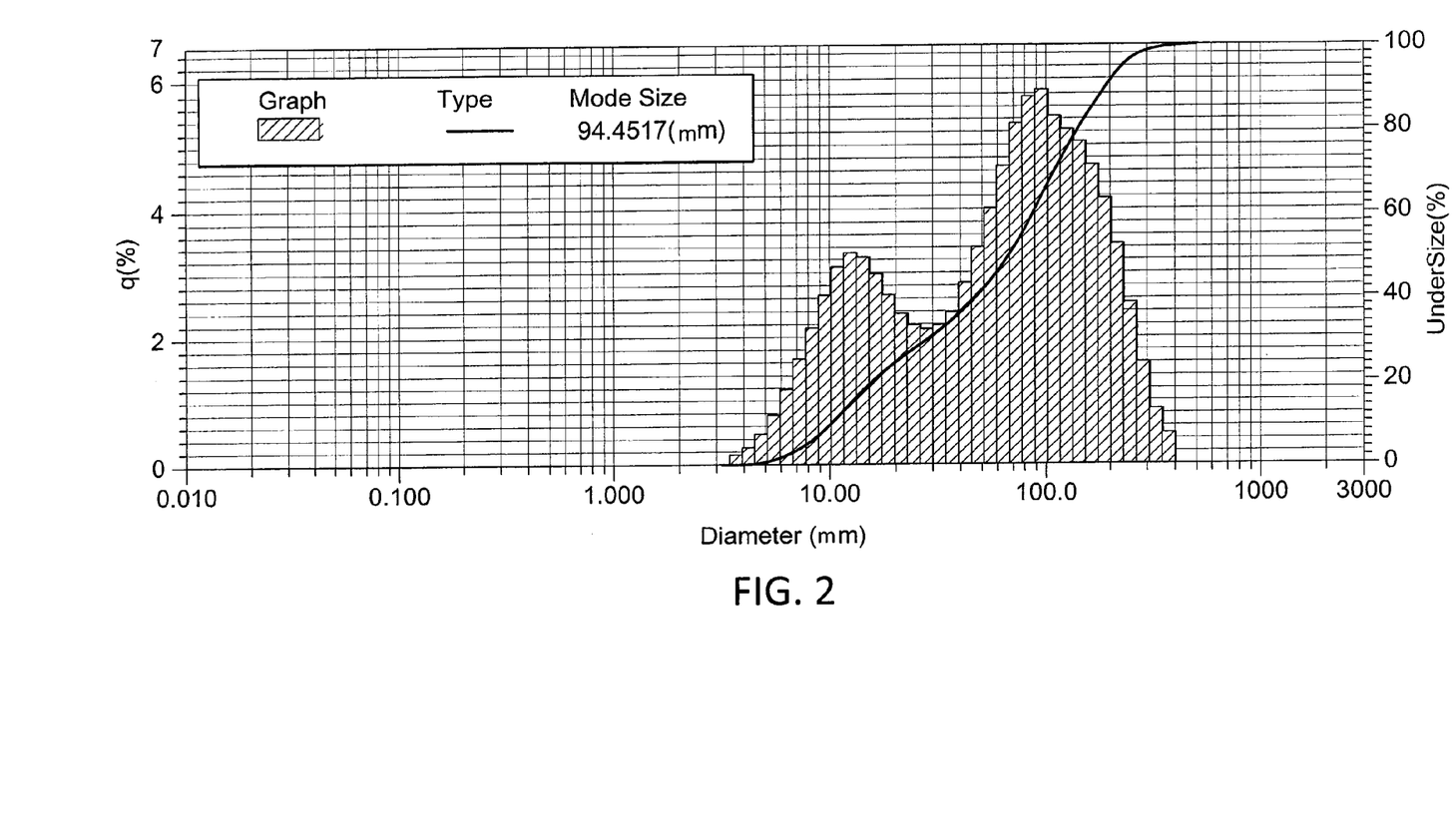
FIG. 2 depicts precipitate particle size distribution obtained from the olefin oligomerization reaction of Example 1, in which aluminum oxide (alumina) sorbent particles with a nominal particle size of 100-200 μm were added.

Introduction of Sorbent Particles and Formation of Precipitate:

After 60 minutes, the reaction mixture from the oligomerization reactor was removed from the reactor as an effluent stream. The effluent stream was cooled to 80° C. and mixed with a suspension in 10 mL of undecane of 1 g of aluminum oxide (alumina) with a nominal particle size of 100-200 μm, in the absence of air. The mixture was then cooled to room temperature by ambient air. The alumina had a moisture content between 5% and 10%, by weight. A quantity of alumina precipitate settled quickly, within 20 seconds. In 2 minutes a discoloration of the solution and formation of additional fluffy yellow precipitate was observed, which settled completely within 5 minutes. The overall quantity of precipitate formed was inhomogeneous. The particle size distribution of the overall quantity of precipitate was then determined, as depicted in FIG. 2. As shown in FIG. 2, the precipitate of Example 1 had a bimodal particle size distribution and a mode particle size of about 94 μm. A bimodal distribution was observed due to the presence of two distinct types of particles: a first type of particles with a size from about 5 μm to about 30 μm, which were primarily polymer precipitated directly from solution, and a second type of particles with a size from about 30 μm to about 300 μm, which were primarily sorbent particles with adsorbed polymer, deactivated catalyst, and other impurities. Further details of the sorbent and precipitate of Example 1 are shown in Tables 1 and 2.

Example 2

To begin, a catalyst composition was prepared according to the procedure described in Example 1. The olefin oligomerization reaction (an oligomerization of ethylene) was conducted as in Example 1.

Figure 3:
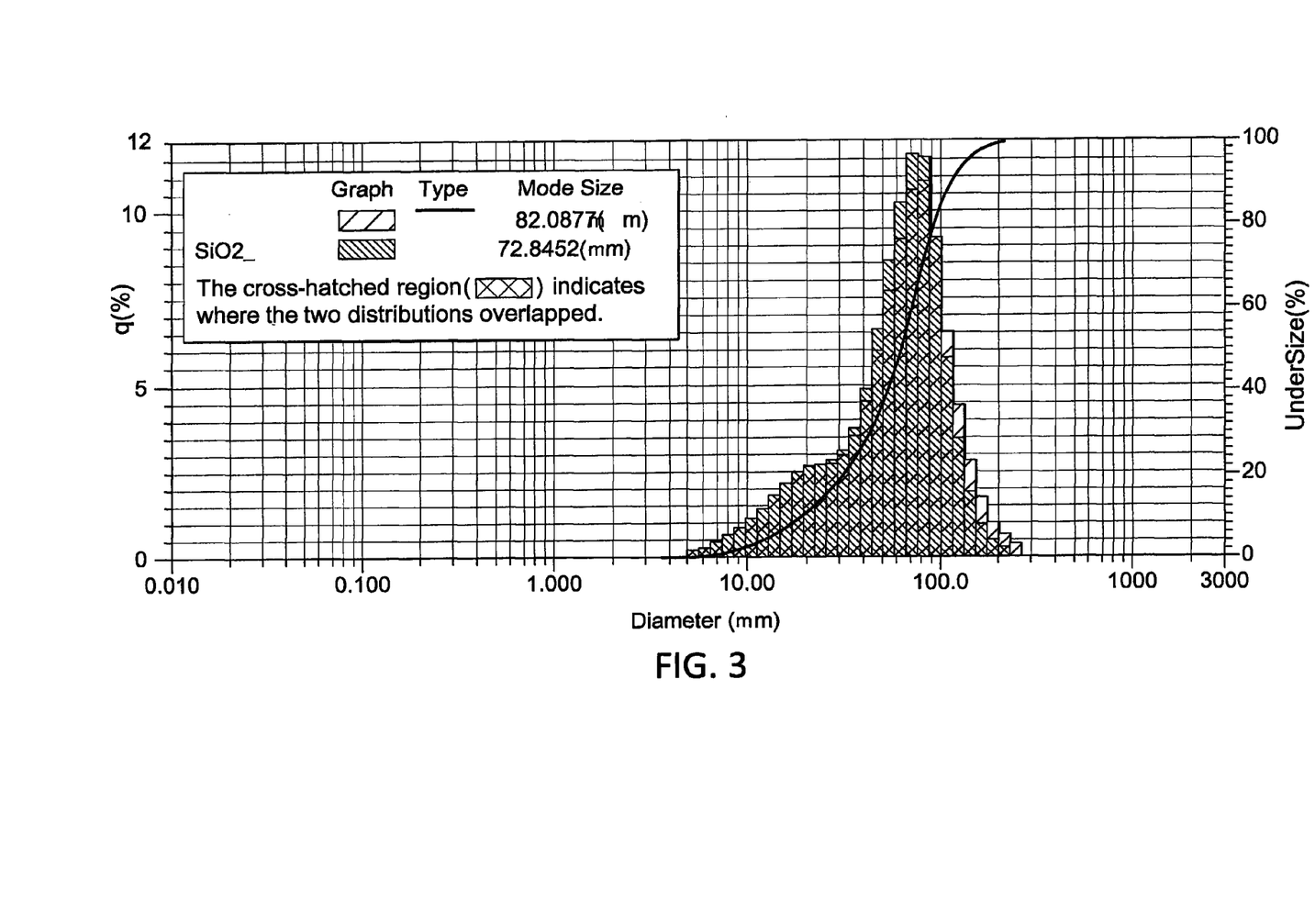
FIG. 3 depicts both sorbent ($SiO_2$) particle size and precipitate (Myr-85-2) particle size distribution obtained from the olefin oligomerization reaction of Example 2, in which silicon oxide (silica) sorbent particles with a nominal particle size of 35-70 μm were added in accordance with the disclosed subject matter.

After 60 minutes, the reaction mixture from the oligomerization reactor was removed from the reactor as an effluent stream and cooled to 75° C. The effluent stream was then mixed with a suspension in 10 mL of undecane of 1 g of silica with a nominal particle size of 35-70 μm, in the absence of air. The mixture was then cooled to room temperature by ambient air. The silica had a moisture content between 5% and 10%, by weight. Discoloration of the solution was observed. Yellow homogeneous precipitate was formed after 2-3 min. The particle size distribution of the overall quantity of precipitate was then determined, as depicted in FIG. 3. One distribution in FIG. 3 shows the particle size of the silica sorbent before addition to the effluent stream ($SiO_2$), while a second distribution in FIG. 3 shows the particle size of the resulting precipitate (Myr-85-2). The cross-hatched region of FIG. 3 indicates where the two distributions overlapped. As shown in FIG. 3, the silica sorbent used in Example 2 had a mode particle size of about 73 μm, while the precipitate of Example 2 had a mode particle size of about 82 μm. Further details of the sorbent and precipitate of Example 2 are shown in Tables 1 and 2.

Example 3

Figure 4:
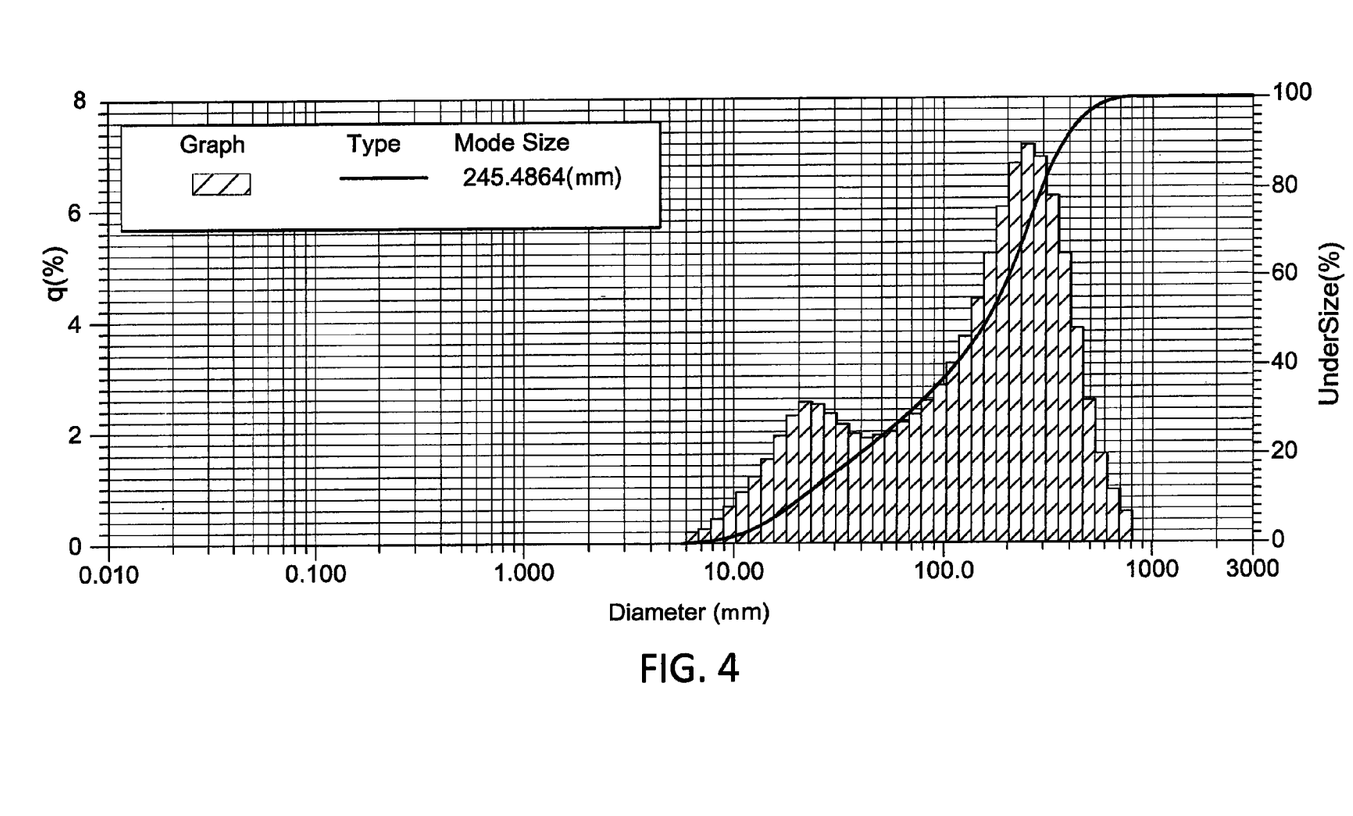
FIG. 4 depicts precipitate particle size distribution obtained from the olefin oligomerization reaction of Example 3, in which silicon oxide (silica) sorbent particles with a nominal particle size of 35-70 μm were added in accordance with the disclosed subject matter.

Catalyst Preparation:
A catalyst composition residue was prepared as in Example 1, and then diluted with cyclohexane to provide a catalyst solution with a concentration of 10 mg Cr/L.
Oligomerization Reaction:
An ethylene oligomerization reaction was carried out in a 2 liter continuous flow stirred tank reactor equipped with a stirrer, with maintenance of the level of the reaction mixture at 50% of the reactor volume. The reactor temperature was maintained at 100° C. by heating with a thermostatic jacket around the reactor. Catalyst solution (10 mg Cr/L, dosed at 0.4 L/h), cyclohexane (dosed at 2.0 L/h), hydrogen (30 mL/min.), and ethylene (with a changing dosage rate to maintain a total reactor pressure of 14 bar) were fed into the reactor. The mean residence time was 20 to 30 minutes, and the total experiment time was 4 hours.
Introduction of Sorbent Particles and Formation of Precipitate:
After the designated reaction period, the reaction mixture from the oligomerization reactor was removed from the reactor as an effluent stream and mixed, at about 100° C., with a suspension in cyclohexane of silicon oxide (silica) with an nominal particle size of 35-70 μm. The suspension was prepared such that it contained 2% silica, by weight. The silica had a moisture content of not more than 10% by weight. The suspension was maintained by stirring the mixture. The effluent stream from the oligomerization reactor (2.5 kg/h) was continuously mixed with a flow of the silica suspension in cyclohexane (0.3 kg/h). The resulting combined flow was sent into a tank cooled to about 40-50° C. with the use of an external jacket. The clarified liquid from the liquid-filled tank was sent to a degasser through a pressure-reducing valve to relieve pressure. After 4 hours, the feeds of effluent stream and silica suspension were stopped, and accumulated precipitate was discharged through a bottom valve. The settling time was about 1 hour. The particle size distribution of the precipitate was then determined, as depicted in FIG. 4. As shown in FIG. 4, the precipitate of Example 3 had a bimodal particle size distribution and a mode particle size of about 245 μm. A bimodal distribution was observed due to the presence of two distinct types of particles: a first type of particles with a size from about 10 μm to about 40 μm, which were sorbent particles with adsorbed polymer, deactivated catalyst, and other impurities, and a second type of particles with a size from about 40 μm to about 500 μm, which included agglomerations of sorbent particles with adsorbed polymer, deactivated catalyst, and other impurities. Further details of the sorbent and precipitate of Example 3 are shown in Tables 1 and 2.

Example 4

A catalyst composition was prepared according to the procedure described in Example 1. The olefin oligomerization reaction (an oligomerization of ethylene) was conducted as in Example 1.

Figure 5:
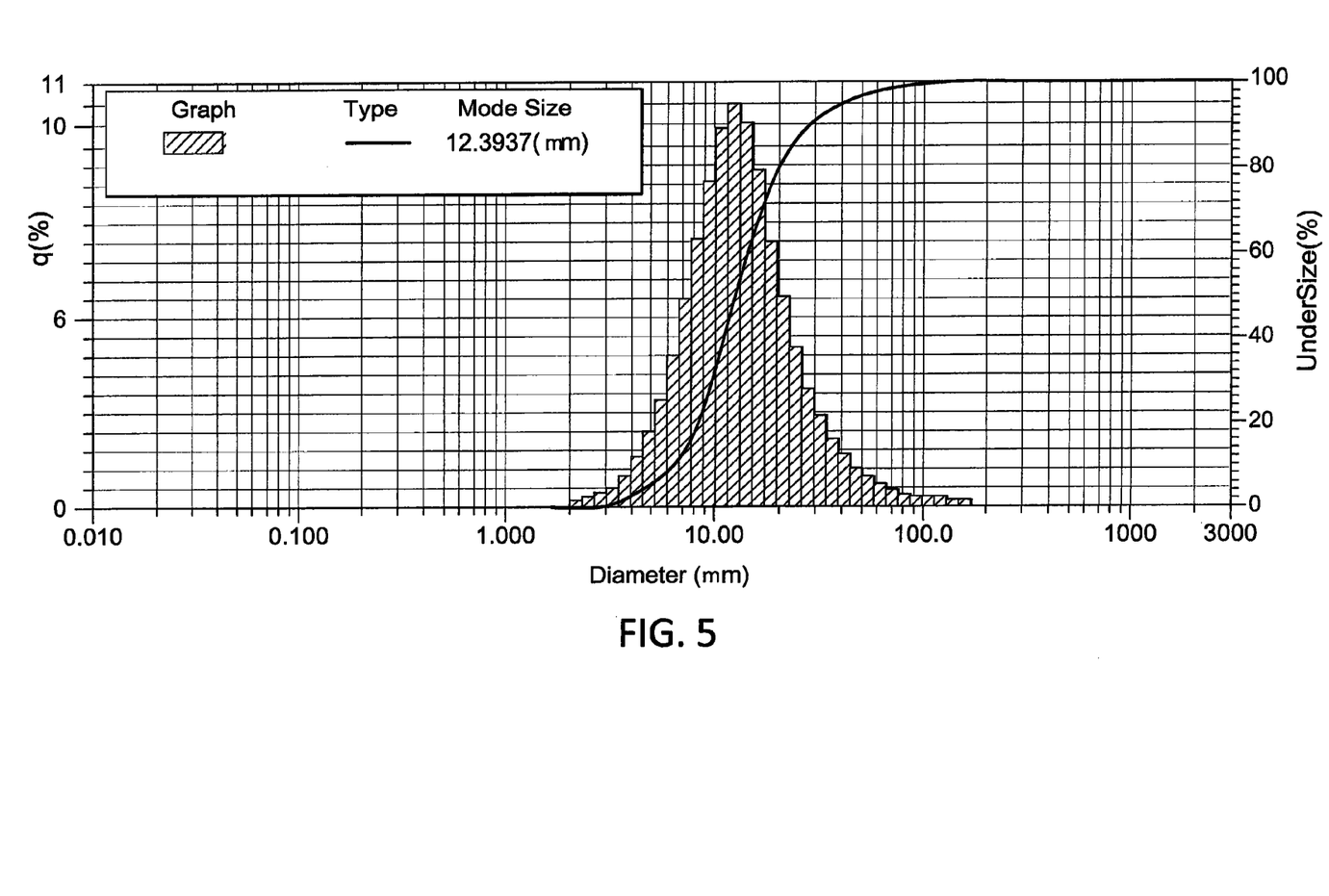
FIG. 5 depicts precipitate particle size distribution obtained from the olefin oligomerization reaction of Example 4, a control experiment in which water was added to deactivate the organometallic catalyst but to which a sorbent was not added.

After 60 minutes, 470 g of the reaction mixture from the oligomerization reactor was removed from the reactor as an effluent stream and cooled to 75° C. The effluent stream was then mixed with 1 mL of water, and the mixture was cooled to room temperature by ambient air. No sorbent was added. Turbidity and yellowing of the solution were observed. After 1-2 minutes, formation of a fine, yellowish precipitate was observed. The precipitate was very slow to settle. The particle size distribution of the precipitate was then determined, as depicted in FIG. 5. As shown in FIG. 5, the precipitate of Example 4 had a mode particle size of about 12 μm. Further details of the precipitate of Example 4 are shown in Table 2.

Table 1 compares the properties of sorbents used in Examples 1-4. "n.m." means not measured.

TABLE 1

| | Properties of sorbents from Examples 1-4. | | | |
|---|---|---|---|---|
| | Fraction of sorbent particles with particle size between 10 and 60 μm, % | Fraction of sorbent particles with particle size between 30 and 60 μm, % | Fraction of sorbent particles with particle size between 60 and 100 μm, % | Fraction of sorbent particles with particle size between 100 and 200 μm, % |
| Example 1 | 6 | n.m. | n.m. | n.m. |
| Example 2 | 40 | 14 | 40 | 17 |

TABLE 1-continued

Properties of sorbents from Examples 1-4.

|  | Fraction of sorbent particles with particle size between 10 and 60 μm, % | Fraction of sorbent particles with particle size between 30 and 60 μm, % | Fraction of sorbent particles with particle size between 60 and 100 μm, % | Fraction of sorbent particles with particle size between 100 and 200 μm, % |
| --- | --- | --- | --- | --- |
| Example 3 | 40 | 14 | 40 | 17 |
| Example 4 | no sorbent added | no sorbent added | no sorbent added | no sorbent added |

Table 2 compares the properties of precipitates in Examples 1-4.

TABLE 2

Properties of precipitates from Examples 1-4.

|  | Fraction of precipitate particles with particle size <5 μm, % | Fraction of precipitate particles with particle size between 5 and 10 μm, % | Fraction of precipitate particles with particle size between 10 and 20 μm, % | Fraction of precipitate particles with particle size >100 μm |
| --- | --- | --- | --- | --- |
| Example 1 | 0.9 | 8.1 | 16.2 | 33.2 |
| Example 2 | 0.0 | 0.8 | 10.0 | 17.2 |
| Example 3 | 0.0 | 1.4 | 7.7 | 64 |
| Example 4 | 5.0 | 27.5 | 45.7 | 0.6 |

For the purpose of illustration, Table 1 indicates that the sorbent used in Example 1 (alumina with a nominal particle size of 100-200 μm) contained a relatively small fraction (6%) of particles with particle size between 10 and 60 μm. These large sorbent particles settled quickly rather than remaining suspended in the effluent stream, which prevented the sorbent from removing optimal quantities of polymer and deactivated catalyst from the effluent stream. As a result, significant quantities of polymer and deactivated catalyst precipitated without adsorption onto the sorbent, resulting in inhomogeneous precipitate that included significant quantities of fluffy precipitate. The inhomogeneous precipitate included significant quantities of precipitate with a particle size of less than 5 μm (0.9%) and precipitate with a particle size between 5 and 10 μm (8.1%). Such small precipitate particles can cause problems, e.g., delay in settling, clogging of filtration devices, and/or passage through filtration devices and contamination of downstream lines and products.

By contrast, the sorbent used in Examples 2 and 3 (i.e., silica with a nominal particle size of 35-70 μm, wherein about 40% of the particles had a particle size between 10 and 60 μm) in accordance with the disclosed subject matter contained a relatively large fraction (40%) of particles with particle size between 10 and 60 μm. Sorbent particles within this size range do not settle immediately and can effectively adsorb polymer (e.g., polyethylene) and deactivated catalyst (e.g., hydrated chromium oxides and hydrated aluminum oxides) to form relatively large precipitate particles, with a particle size of 10 μm or greater. Such particles can readily be removed by filtration. In Examples 2 and 3, the precipitate formed after introduction of the sorbent included no precipitate with a particle size of less than 5 μm and only small quantities (less than 1.5%) of precipitate with a particle size between 5 μm and 10 μm.

While the same sorbent was used in Examples 2 and 3, the precipitates obtained from the two Examples have different size distributions. These differences can be attributed to various differences in experimental procedure, e.g., differences in experimental setup, solvent, cooling processes, temperature at which the sorbent was added, and settling time. However, despite differences in experimental procedure, both Examples 2 and 3 had improved precipitate properties as compared to Examples 1 and 4. In Examples 2 and 3, 40% of the sorbent particles had a particle size between 10 μm and 60 μm, whereas in Example 1 only 6% of the sorbent particles had a particle size between 10 μm and 60 μm. The water content of the sorbents was comparable among Examples 1, 2, and 3. As a result of the large fraction (40%) of particles with particle size between 10 and 60 μm in Examples 2 and 3, much less small precipitate (i.e., precipitate with a particle size less than 10 μm) was formed as compared to Example 1.

No sorbent was used in Example 4. Without a sorbent to adsorb polymer and deactivated catalyst (e.g., hydrated metal oxides), these materials precipitated in a fine, slow-to-settle precipitate. The precipitate included significant quantities of precipitate with a particle size of less than 5 μm (5.0%) and precipitate with a particle size between 5 and 10 μm (27.5%). Such small precipitate particles can cause problems, e.g., delay in settling, clogging of filtration devices, and/or passage through filtration devices and contamination of downstream lines and products.

Accordingly, byproducts and side products (polymer and deactivated catalyst) could be more effectively removed from the effluent streams of Examples 2 and 3 as compared to the effluent streams of Examples 1 and 4, providing improved simplicity of operation, improved efficiency, and improved product purity. Additional advantages include faster filtration rates, lower pressure drops over filters, and improved removal of trace impurities (e.g., pyrrole compounds and metals). As specifically embodied in Examples 2 and 3, the methods of the present disclosure do not require addition of a deactivating agent separate from the sorbent itself.

Additional Embodiments

Additionally or alternatively, the disclosed subject matter can include one or more of the following embodiments:

Embodiment 1

A method of precipitating polymer and deactivated organometallic catalyst in an olefin oligomerization reaction, including providing an effluent stream from an olefin oligomerization reaction, wherein the effluent stream includes a polymer and an organometallic catalyst, introducing sorbent particles into the effluent stream, wherein the sorbent particles include a deactivating agent selected from the group consisting of water, alcohols, amines, amino alcohols, and combinations thereof and wherein at least about 10% of the sorbent particles have a particle size in a range from 10 µm to 60 µm, and cooling the effluent stream, thereby precipitating polymer and deactivated organometallic catalyst from the effluent stream to provide a precipitate including sorbent, polymer, and deactivated catalyst.

Embodiment 2

The method of the foregoing Embodiment, wherein the organometallic catalyst includes chromium.

Embodiment 3

The method of any of the foregoing Embodiments, wherein the olefin oligomerization reaction includes a trimerization of ethylene to 1-hexene.

Embodiment 4

The method of any of the foregoing Embodiments, wherein the sorbent particles include particles selected from the group consisting of alumina particles, silica particles, and combinations thereof.

Embodiment 5

The method of any of the foregoing Embodiments, wherein at least about 20% of the sorbent particles have a particle size in a range from 10 µm to 60 µm.

Embodiment 6

The method of any of the foregoing Embodiments, wherein about 40% of the sorbent particles have a particle size in a range from 10 µm to 60 µm.

Embodiment 7

The method of any of the foregoing Embodiments, wherein the sorbent particles include the deactivating agent in an amount less than about 20% by weight.

Embodiment 8

The method of any of the foregoing Embodiments, wherein the sorbent particles include the deactivating agent in an amount between about 5% and about 10% by weight.

Embodiment 9

The method of any of the foregoing Embodiments, wherein the sorbent particles have a surface area greater than 10 $m^2/g$.

Embodiment 10

The method of any of the foregoing Embodiments, wherein the sorbent particles are introduced into the effluent stream as a suspension in a solvent.

Embodiment 11

The method of any of the foregoing Embodiments, wherein the sorbent particles are introduced into the effluent stream in an amount between about 0.1 g and about 1.0 g of the sorbent particles per 1 kg of the effluent stream.

Embodiment 12

The method of any of the foregoing Embodiments, wherein the deactivating agent includes water.

Embodiment 13

The method of any of the foregoing Embodiments, wherein the effluent stream is cooled at about the same time that the sorbent particles are introduced into the effluent stream.

Embodiment 14

The method of any of the foregoing Embodiments, wherein the effluent stream is cooled after the sorbent particles are introduced into the effluent stream.

Embodiment 15

The method of any of the foregoing Embodiments, wherein the precipitate includes precipitate particles having a particle size in a range from about 1 µm to about 1000 µm.

Embodiment 16

The method of any of the foregoing Embodiments, wherein less than about 8% of the precipitate particles have a particle size of less than 10 µm.

Embodiment 17

The method of any of the foregoing Embodiments, wherein less than about 0.8% of the precipitate particles have a particle size of less than 5 µm.

Embodiment 18

The method of any of the foregoing Embodiments, further including separating the precipitate from the effluent stream to provide a purified product.

Embodiment 19

The method of any of the foregoing Embodiments, combined with the method of any other Embodiment.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

While the disclosed subject matter is described herein in terms of preferred embodiments, those skilled in the art will recognize that various modifications and improvements can be made to the disclosed subject matter without departing from the scope thereof. Moreover, although individual features of some embodiments of the disclosed subject matter can be discussed herein or shown in the drawings of those embodiments and not in other embodiments, it should be apparent that individual features of some embodiments can be combined with one or more features of another embodiment or features from a plurality of embodiments.

What is claimed is:

1. A method of precipitating polymer and deactivated organometallic catalyst in an olefin oligomerization reaction, comprising:
    providing an effluent stream from an olefin oligomerization reaction, wherein the effluent stream comprises a polymer and an organometallic catalyst;
    introducing sorbent particles into the effluent stream, wherein the sorbent particles comprise a deactivating agent selected from the group consisting of water, alcohols, amines, amino alcohols, and combinations thereof and wherein at least about 10% of the sorbent particles have a particle size in a range from 10 μm to 60 μm; and
    cooling the effluent stream, thereby precipitating polymer and deactivated organometallic catalyst from the effluent stream to provide a precipitate comprising sorbent, polymer, and deactivated catalyst.

2. The method of claim 1, wherein the organometallic catalyst comprises chromium.

3. The method of claim 1, wherein the olefin oligomerization reaction comprises a trimerization of ethylene to 1-hexene.

4. The method of claim 1, wherein the sorbent particles comprise particles selected from the group consisting of alumina particles, silica particles, and combinations thereof.

5. The method of claim 1, wherein at least about 20% of the sorbent particles have a particle size in a range from 10 μm to 60 μm.

6. The method of claim 5, wherein about 40% of the sorbent particles have a particle size in the range from 10 μm to 60 μm.

7. The method of claim 1, wherein the sorbent particles comprise the deactivating agent in an amount less than about 20% by weight.

8. The method of claim 7, wherein the sorbent particles comprise the deactivating agent in an amount between about 5% and about 10% by weight.

9. The method of claim 1, wherein the sorbent particles have a surface area greater than 10 $m^2/g$.

10. The method of claim 1, wherein the sorbent particles are introduced into the effluent stream as a suspension in a solvent.

11. The method of claim 1, wherein the sorbent particles are introduced into the effluent stream in an amount between about 0.1 g and about 1.0 g of the sorbent particles per 1 kg of the effluent stream.

12. The method of claim 1, wherein the deactivating agent comprises water.

13. The method of claim 1, wherein the effluent stream is cooled at about the same time that the sorbent particles are introduced into the effluent stream.

14. The method of claim 1, wherein the effluent stream is cooled after the sorbent particles are introduced into the effluent stream.

15. The method of claim 1, wherein the precipitate comprises precipitate particles having a particle size in a range from about 1 μm to about 1000 μm.

16. The method of claim 15, wherein less than about 8% of the precipitate particles have a particle size of less than 10 μm.

17. The method of claim 15, wherein less than about 0.8% of the precipitate particles have a particle size of less than 5 μm.

18. The method of claim 1, further comprising separating the precipitate from the effluent stream to provide a purified product.

* * * * *

UNITED STATES PATENT AND TRADEMARK OFFICE
CERTIFICATE OF CORRECTION

PATENT NO. : 9,975,822 B2  
APPLICATION NO. : 15/539134  
DATED : May 22, 2018  
INVENTOR(S) : Timur Mikhailovich Zilbershtein

Page 1 of 1

It is certified that error appears in the above-identified patent and that said Letters Patent is hereby corrected as shown below:

On the Title Page

Please add:
(73) Assignee: PUBLIC JOINT STOCK COMPANY "SIBUR HOLDING", Tobolsk (RU)

Signed and Sealed this  
Third Day of July, 2018

Andrei Iancu  
*Director of the United States Patent and Trademark Office*